(12) United States Patent
Brown et al.

(10) Patent No.: US 10,472,676 B2
(45) Date of Patent: Nov. 12, 2019

(54) COMPOSITIONS FOR USE IN SECURITY MARKING

(75) Inventors: Jason Brown, Locksbottom (GB); Bas Reichert, Leiden (NL)

(73) Assignee: Selectamark Security Systems PLC, Locksbottom Kent (GB)

( * ) Notice: Subject to any disclaimer, the term of this patent is extended or adjusted under 35 U.S.C. 154(b) by 189 days.

(21) Appl. No.: 13/265,758

(22) PCT Filed: Apr. 23, 2010

(86) PCT No.: PCT/EP2010/055473
§ 371 (c)(1),
(2), (4) Date: Feb. 14, 2012

(87) PCT Pub. No.: WO2010/122159
PCT Pub. Date: Oct. 28, 2010

(65) Prior Publication Data
US 2012/0135413 A1    May 31, 2012

(30) Foreign Application Priority Data

Apr. 24, 2009   (GB) .................................. 0907100.2

(51) Int. Cl.
*C12Q 1/68*      (2018.01)
*C12Q 1/6876*    (2018.01)
*C12Q 1/6813*    (2018.01)

(52) U.S. Cl.
CPC ......... *C12Q 1/6876* (2013.01); *C12Q 1/6813* (2013.01)

(58) Field of Classification Search
USPC ....................................................... 435/6.12
See application file for complete search history.

(56) References Cited

U.S. PATENT DOCUMENTS

| | | |
|---|---|---|
| 1,606,258 A | 11/1926 | Morssen |
| 3,344,757 A | 10/1967 | Touyet |
| 3,454,567 A | 7/1969 | Klopping et al. |
| 3,564,525 A | 2/1971 | Birchfield |
| 3,730,110 A | 5/1973 | Peters |
| 3,740,402 A | 6/1973 | Cevasco et al. |
| 3,861,886 A | 1/1975 | Meloy |
| 3,915,886 A | 10/1975 | Molina |
| 3,960,755 A | 6/1976 | Beachem et al. |
| 4,131,064 A | 12/1978 | Ryan et al. |
| 4,197,104 A | 4/1980 | Krystyniak et al. |
| 4,198,307 A | 4/1980 | Berkowitz et al. |
| 4,226,194 A | 10/1980 | Grahn |
| 4,329,393 A | 5/1982 | LaPerre et al. |
| 4,399,226 A | 8/1983 | Danielson et al. |
| 4,441,943 A | 4/1984 | Kydd |
| 4,480,177 A | 10/1984 | Allen |
| 4,591,548 A | 5/1986 | Delprato |
| 4,610,806 A | 9/1986 | Rosen |
| 4,764,290 A | 8/1988 | Currey |
| 4,767,205 A | 8/1988 | Schwartz et al. |
| 4,793,644 A | 12/1988 | Swift |
| 4,841,752 A | 6/1989 | Fletcher |
| 4,858,465 A | 8/1989 | Molina |
| 5,061,310 A | 10/1991 | Ooms et al. |
| 5,079,284 A | 1/1992 | Nakane et al. |
| 5,084,097 A | 1/1992 | McCreary et al. |
| 5,135,568 A | 8/1992 | Fasano |
| 5,139,812 A * | 8/1992 | Lebacq ................. B82Y 10/00 118/201 |
| 5,149,138 A | 9/1992 | Zemsky |
| 5,208,085 A | 5/1993 | Pace |
| 5,294,664 A | 3/1994 | Morrison, Jr. et al. |
| 5,360,628 A | 11/1994 | Butland |
| 5,405,599 A | 4/1995 | Porrovecchio |
| 5,451,505 A * | 9/1995 | Dollinger .............. C06B 23/008 435/6.11 |
| 5,599,578 A | 2/1997 | Butland |
| 5,605,650 A | 2/1997 | Cleary |
| 5,776,737 A * | 7/1998 | Dunn ..................... C12N 15/10 250/458.1 |
| 5,811,152 A | 9/1998 | Cleary |
| 5,928,954 A | 7/1999 | Rutledge et al. |
| 5,953,799 A | 9/1999 | Seidel |
| 6,274,381 B1 | 8/2001 | Pauls et al. |
| 6,312,911 B1 * | 11/2001 | Bancroft ................ B82Y 10/00 435/6.11 |
| 6,402,986 B1 | 6/2002 | Jones, II et al. |
| 6,544,739 B1 * | 4/2003 | Fodor .................. B01J 19/0046 435/252.3 |
| 7,079,230 B1 | 7/2006 | McInerney et al. |
| 7,118,751 B1 * | 10/2006 | Ledbetter ............... A61K 39/00 424/192.1 |
| 7,148,066 B2 | 12/2006 | Bickett et al. |
| 7,488,954 B2 | 2/2009 | Ross et al. |
| 8,415,165 B2 * | 4/2013 | Liang .................. C09D 7/1233 252/582 |

(Continued)

FOREIGN PATENT DOCUMENTS

| | | |
|---|---|---|
| EP | 0116273 A1 | 1/1984 |
| EP | 0327163 A2 | 1/1989 |

(Continued)

OTHER PUBLICATIONS

International preliminary report on patentability (IPRP) for PCT/EP2010/055473 (WO2010-122159) filed on Apr. 23, 2010.*

(Continued)

*Primary Examiner* — Samuel C Woolwine
(74) *Attorney, Agent, or Firm* — Gavrilovich, Dodd & Lindsey LLP

(57) ABSTRACT

A composition comprising: a plurality of identical first synthetic nucleotide oligomers; and a plurality of identical second synthetic nucleotide oligomers which are different to the first synthetic nucleotide oligomers, wherein each of the first synthetic nucleotide oligomers comprises a first primer binding sequence of bases, a first identifier sequence of three to seven bases in length, and a second primer binding sequence of bases, the first identifier sequence being disposed between the first and second primer binding sequences, wherein each of the second synthetic nucleotide oligomers comprises a third primer binding sequence of bases, a second identifier sequence of three to seven bases in length, and a fourth primer binding sequence of bases, the second identifier sequence being disposed between the third and fourth primer binding sequences, and wherein the first identifier sequence is different to the second identifier sequence.

15 Claims, 3 Drawing Sheets

(56) References Cited

U.S. PATENT DOCUMENTS

| | | | |
|---|---|---|---|
| 2002/0146698 A1 | 10/2002 | Dephillipo et al. | |
| 2003/0044786 A1* | 3/2003 | Coticone | C12Q 1/6848 435/6.12 |
| 2003/0179902 A1 | 9/2003 | Ambrogio et al. | |
| 2003/0235836 A1 | 12/2003 | Simonetta et al. | |
| 2004/0023207 A1* | 2/2004 | Polansky | A61K 31/00 435/5 |
| 2004/0166520 A1* | 8/2004 | Connolly | C12Q 1/6825 435/6.12 |
| 2005/0001059 A1 | 1/2005 | Yang | |
| 2005/0026181 A1 | 2/2005 | Davis et al. | |
| 2005/0250101 A1 | 11/2005 | Gil et al. | |
| 2006/0073506 A1* | 4/2006 | Christians | C12Q 1/6813 435/6.11 |
| 2006/0286569 A1 | 12/2006 | Bar-Or et al. | |
| 2007/0009925 A1* | 1/2007 | Fang | C12Q 1/6827 435/6.12 |
| 2007/0072212 A1* | 3/2007 | Vinayagamoorthy | C12Q 1/686 435/6.18 |
| 2007/0077562 A1* | 4/2007 | Hossain | C12N 15/1003 435/6.16 |
| 2009/0037739 A1* | 2/2009 | Silverbrook | G06Q 10/087 713/176 |
| 2009/0075261 A1* | 3/2009 | Hayward | C09D 7/1233 435/6.11 |
| 2012/0135413 A1 | 5/2012 | Brown et al. | |

FOREIGN PATENT DOCUMENTS

| | | | | |
|---|---|---|---|---|
| GB | 2245583 A | | 1/1992 | |
| GB | 2319337 A | | 5/1998 | |
| GB | 2387437 A | | 10/2003 | |
| GB | 2430469 A | | 3/2007 | |
| GB | 2458281 | * | 9/2009 | G08B 15/02 |
| GB | 2472371 B | | 10/2011 | |
| WO | WO1991014441 | * | 11/1990 | C12Q 1/68 |
| WO | 9307233 A1 | | 4/1993 | |
| WO | 9315398 A1 | | 8/1993 | |
| WO | 00/45401 A | | 8/2000 | |
| WO | WO2000061799 | * | 10/2000 | C12Q 1/68 |
| WO | 01/36676 A | | 5/2001 | |
| WO | WO01/36676 | * | 5/2001 | C12Q 1/68 |
| WO | 02/66678 A | | 8/2002 | |
| WO | WO02/066678 | * | 8/2002 | C12Q 1/68 |
| WO | WO2002090581 | * | 11/2002 | C12Q 1/68 |
| WO | 03/74733 A2 | | 9/2003 | |
| WO | WO03/074733 | * | 9/2003 | C12Q 1/68 |
| WO | 03/80931 A1 | | 10/2003 | |
| WO | WO03/080931 | * | 10/2003 | D21H 21/46 |
| WO | 05/111212 A2 | | 11/2005 | |
| WO | WO2005/111212 | * | 11/2005 | C12N 15/11 |
| WO | WO2005118847 | * | 12/2005 | C12Q 1/68 |
| WO | WO2007086890 | * | 8/2007 | C12Q 1/68 |
| WO | WO2007114693 | * | 10/2007 | C12Q 1/68 |
| WO | 2010122159 A1 | | 10/2010 | |

OTHER PUBLICATIONS

Meyer M, Stenzel U, Hofreiter M. Parallel tagged sequencing on the 454 platform. Nat Protoc. 2008;3(2):267-78.*

Hamady M, Walker JJ, Harris JK, Gold NJ, Knight R. Error-correcting barcoded primers for pyrosequencing hundreds of samples in multiplex. Nat Methods. Mar. 2008; 5(3):235-7. Epub Feb. 10, 2008.*

Haff LA, Smirnov IP. Multiplex genotyping of PCR products with MassTag-labeled primers. Nucleic Acids Res. Sep. 15, 1997; 25(18):3749-50.*

Binladen J, Gilbert MT, Bollback JP, Panitz F, Bendixen C, Nielsen R, Willerslev E. The use of coded PCR primers enables high-throughput sequencing of multiple homolog amplification products by 454 parallel sequencing. PLoS One. Feb. 14, 2007; 2(2):e197: pp. 1-9.*

Hoffmann C, Minkah N, Leipzig J, Wang G, Arens MQ, Tebas P, Bushman FD. DNA bar coding and pyrosequencing to identify rare HIV drug resistance mutations. Nucleic Acids Res. 2007;35(13):e91: pp. 1-8. Epub Jun. 18, 2007.*

Sutcliffe J. pBR322 restriction map derived from the DNA sequence: accurate DNA size markers up to 4361 nucleotide pairs long. Nucleic Acids Research 5(8):2721-2728 (1978).*

Dinham, Rowena, Combined Search and Examination Report, GB0907100.2, Intellectual Property Office, dated Aug. 19, 2009.

Barz, Wolfgang, International Search Report, PCT/EP2010/055473, European Patent Office, dated Aug. 4, 2010.

Maria Gabriela Cabrera Valladares, Office Action issued in Patent Application No. MX/2014/20598, Mexican Patent Office, dated Mar. 6, 2014.

Plumb, Claire, Office Action, Canadian Intellectual Property Office, Application No. 2,759,831, dated Mar. 7, 2016.

* cited by examiner

COMPOSITIONS FOR USE IN SECURITY MARKING

CROSS REFERENCE TO RELATED APPLICATIONS

This application is a U.S. National Stage Application filed under 35 U.S.C. § 371 and claims priority to International Application No. PCT/EP2010/055473, filed Apr. 23, 2010, which application claims priority to Great Britain Application No. 0907100.2, filed Apr. 24, 2009, the disclosures of which are incorporated herein by reference.

FIELD OF THE INVENTION

The present invention relates to synthetic nucleotide containing compositions, methods of manufacturing said compositions, use of the compositions in security marking of property and/or for marking a thief or attacker, and methods of detecting such a composition on a person or property and analysing the composition to determine the origin of the composition and/or information about the owner of the property.

BACKGROUND OF THE INVENTION

Synthetic nucleotide containing compositions for use in security marking of property and/or for marking a thief or attacker are known in the art. Indeed, the present applicant has already developed and marketed several products containing such compositions. Some examples of the present applicant's products which utilize such compositions are discussed below.

The SelectaDNA® property marking kit comprises a pot of adhesive which can be applied to property using an applicator in order to mark the property with a unique composition which can be traced back to the owner in the event of the property being stolen by a thief and then retrieved by the police. Each pot of adhesive contains a unique DNA composition and also several thousand microdots dispersed throughout the adhesive. Each microdot contains a unique registration code and a database telephone number or internet address. A database is maintained by a service provider linking each unique registration code to details of the owner of the property, e.g. name, address and/or telephone number of the owner. These details may be obtained when an owner of the property purchases the property marking kit and entered into the database. This database, or a second database, also contains information about the unique DNA composition which is either linked to the registration code or directly to the owner's details. The adhesive also contains a fluorescent material which emits visible light under UV light in order to allow the adhesive marking on the property to be readily located by the police.

When a stolen item of property is recovered by the police a UV lamp can be utilized to locate the adhesive marking on the property. Using a magnifying glass a microdot can be located within the adhesive marking and the unique registration code and a database telephone number or internet address can be read. The police can then phone the database telephone number and an operator of the database can use the unique registration code to provide details of the owner of the property such that the police can contact the owner and return the property. If the police can't locate a microdot in the adhesive marking then a small sample of the adhesive can be removed and sent to a laboratory for analysis to obtain information about the unique DNA composition dispersed throughout the adhesive. This information can then be used to identify the owner using the database. A sticker or other marking on the property can indicate a telephone number or internet address which the police may use to contact the database operator in the absence of any microdots.

The aforementioned kit thus provides two possible methods for tracing the owner of stolen property, via the microdots or via the unique DNA composition. However, it is of course envisaged by the present applicant that either one of these methods may be used on there own. Indeed, for some applications it may not be appropriate to provide microdots in a security marking composition. For example, it may not be appropriate to provide microdots in compositions which are to be expelled as an aerosol to mark a thief or attacker as such microdots may block the dispensing nozzle and/or be readily washed off.

Such is the case for the present applicant's DNA PERSONAL ALARM which does not use microdots. This product comprises a hand-held personal alarm in the form of a pressurized container housing a composition which comprises a unique DNA composition and a fluorescent material of the kind used in the previously described property marking kit. As described in relation to the property marking kit, a database is maintained by a service provider linking information about each unique DNA composition to details of the owners of the personal alarms. If an owner is attacked they can spray their attacker using the personal alarm. Subsequently, if apprehended, a UV lamp can be utilized to locate the DNA composition on the attacker. A small sample of the composition can be removed and sent to a laboratory for analysis to obtain information about the unique DNA composition. This information can then be used to identify the owner of the personal alarm using the database. As such, the attacker can be unarguably linked to the attack on the owner of the personal alarm, any stolen property can be returned, and the information used to secure a conviction.

Yet another use of synthetic DNA containing compositions is in building security system, particularly at entry points such as doors and windows. A building security system which dispenses a fluid for deterring and/or identifying an intruder is described in the present applicant's own earlier patent application, GB0804493.5. In this earlier application it is described that a particularly useful formulation comprises a DNA marker/identifier, a UV tracer/fluorescent material, a propellant, and optionally a solvent which may be organic, e.g. an alcohol, or aqueous. As with the aforementioned property marking kit and personal alarm, a database is maintained by a service provider linking information about each unique DNA composition to details of the owners of the security system. If a building is broken into by a burglar, the security system sprays the intruder with the DNA composition. Subsequently, if apprehended, a UV lamp can be utilized to locate the DNA composition on the intruder. A small sample of the composition can be removed and sent to a laboratory for analysis to obtain information about the unique DNA composition. This information can then be used to identify the owner of the building using the database. As such, the intruder can be unarguably linked to the burglary such that any stolen property can be returned and the information used to secure a conviction.

One problem which the present applicant has identified with current products on the market is that the proprietary synthetic DNA used therein requires special Biotage® equipment to analyse the DNA instead of the more commonly used Sanger equipment. The present applicant has realized that there would be a big commercial advantage to enabling the use of standard Sanger equipment because of its wide availability and usage. This would enable the present applicant to sell products, such as the previously described property marking kit, personal alarm and building security system to distributors abroad. Using Biotage® seriously limits commercial opportunities because it is very difficult to find labs that both: (1) have the equipment; and (2) are willing do analysis on a commercial level. Furthermore, the present applicant considers that overseas police forces will want to perform the DNA analysis in their own country for practical, political and/or legal reasons and would not want to rely upon proprietary equipment located in a foreign country.

Another problem which the present applicant has identified is that the synthetic DNA compositions used in current products are not optimized for the security marking applications described herein. In particularly, the present applicant believes that the individual DNA strands in current compositions are overly long. Generally, the longer the DNA strands, the more costly they are to manufacture and the more costly they are to analyze.

It is an aim of the present invention to solve the problems described above.

SUMMARY OF THE INVENTION

According to a first aspect of the present invention there is provided a composition comprising: a plurality of identical first synthetic nucleotide oligomers; and a plurality of identical second synthetic nucleotide oligomers which are different to the first synthetic nucleotide oligomers, wherein each of the first synthetic nucleotide oligomers comprises a first primer binding sequence of bases, a first identifier sequence of three to seven bases in length, and a second primer binding sequence of bases, the first identifier sequence being disposed between the first and second primer binding sequences, wherein each of the second synthetic nucleotide oligomers comprises a third primer binding sequence of bases, a second identifier sequence of three to seven bases in length, and a fourth primer binding sequence of bases, the second identifier sequence being disposed between the third and fourth primer binding sequences, and wherein the first identifier sequence is different to the second identifier sequence.

The composition is a security marking composition, typically (but not exclusively) suitable for marking property and/or people. The property might be property likely to be in danger of being lost or stolen, and the people might be criminals such as thieves, assailants and other attackers, or might be other individuals who might benefit from security marking, such as soldiers. The oligomers are constructed so that they can easily be related to the owner of the composition, using a database. Thus the first and second identifier sequences are relatable to the owner of the composition via a database. The database contains information on the owner of the composition and connects this information to the first and second identifier sequences. Thus the information on the owner can be obtained from identification of the first and second identifier sequences in the composition.

By providing two different synthetic nucleotide oligomers in the composition, the oligomers can be made shorter while still providing a large enough variation to uniquely identify each composition. For example, if both oligomers have an identifier sequence of three bases in length, then there are $(4^3)^2$ possible combinations, i.e. 4096. If both oligomers have an identifier sequence of seven bases in length, then there are $(4^7)^2$ possible combinations, i.e. $2.684 \times 10^8$. The applicant considers that this range of combinations is sufficient to ensure that the compositions used in security marking of property and/or for marking a thief or attacker will be uniquely identifiable. The advantage of using a shorter identifier sequence is that the nucleotide oligomers will be cheaper and easier to manufacture and also cheaper and easier to analyze. The disadvantage is that the number of unique variations is limited. For example, if the lowest end of the claimed range is used (i.e. three bases in each identifier sequence) then after producing and selling 4096 products, any further products will duplicate previous identifiers. This lowest range will be useful for products which are likely to have a low numbers of sales. Alternatively, or additionally, the identifiers may be geographically regionalized, by country for example, such that identifiers can be re-used in different regions. Other groupings may be possible in order to allow re-use of identifier sequences.

Despite the above possibilities to re-use identifier combinations, it would clearly be desirable to provide completely unique worldwide identifiers. Accordingly, it is preferred that one or both of the first and second identifier sequences have at least four bases. If both oligomers have an identifier sequence of four bases in length, then there are $(4^4)^2$ possible combinations, i.e. 65536, which may be sufficient for high-end, low sale volume products such as home security systems.

Similarly, it is unlikely that many products will sell in sufficient volume that $2.684 \times 10^8$ possible variations will be required. Accordingly, for most applications it will be preferable if one or both of the first and second identifier sequences have six bases or less. If both oligomers have an identifier sequence of six bases in length, then there are $(4^6)^2$ possible combinations, i.e. $1.678 \times 10^7$.

If a large number of unique variations are required, it is possible to provide additional nucleotide oligomers rather than increasing the length of the identifier sequences. Accordingly, the composition may comprise a third nucleotide oligomer, the third nucleotide oligomer having a third identifier sequence flanked by primer binding sites. Four or more nucleotide oligomers may also be utilized such that the length of the identifier sequences can be reduced while still maintaining a sufficient range of unique variations. Of course, as an alternative, or in addition, to adding further oligomers, if a larger number of unique variations is required then the length of the identifier sequences of the oligomers in the composition may be increased so as to be greater than seven bases in length. However, this will also increase cost in terms of manufacture and analysis.

The primer binding sequences on either side of the identifier sequences are required for amplifying and sequencing the nucleotide oligomers. According to certain embodiments, the first and second primer binding sequences are different from each other. Similarly, according to certain embodiments the third and fourth primer binding sequences are different from each other. Further still, according to certain embodiments the first and second primer binding sequences are different from the third and fourth primer binding sequences.

According to embodiments of the present inventions, each of the primer binding sequences may be identical or complementary to a portion of a standard PCR (polymerase chain reaction) primer, particularly a terminal portion at the 3' region of a PCR primer. According to certain embodiments, the first and third primer binding sequences are identical to portions of standard primer sequences used in Sanger amplification and sequencing. According to certain embodiments, the second and fourth primer binding sequences are complementary to portions of standard primer sequences used in Sanger amplification and sequencing.

It is preferred that the primer binding sequences should be kept short for ease of manufacture of the oligomers. However, standard sequencers are less accurate for shorter oligomers. The present applicant has realized that short primer binding sequences can be used for the oligomers if, during amplification, longer primer sequences are used to lengthen the oligomers prior to amplification and sequencing. As such, the first, second, third and fourth primer binding sequences may each have a length in the range 5 to 40 bases, more preferably 10 to 30 bases, most preferably 15 to 20 bases. These primer binding sequences are of sufficient length to reliably bind to longer primers prior to standard amplification using a polymerase chain reaction.

In order to keep the nucleotide oligomers as short as possible, it is preferred that each of the first synthetic nucleotide oligomers consists only of the first primer binding sequence, the first identifier sequence, and the second primer binding sequence. Similarly, it is preferred that each of the second synthetic nucleotide oligomers consists only of the third primer binding sequence, the second identifier sequence, and the fourth primer binding sequence.

Compositions according to embodiments of the present invention may comprise further components as described in the background section. For example, compositions may comprise microdots, fluorescent material, adhesive, grease, gel, an organic or aqueous solvent, and/or a propellant. According to one embodiment, the composition comprises an adhesive in which the oligomers are dispersed. According to another embodiment the composition comprises a solvent which renders the composition sprayable. According to this embodiment, a pressurized container may be provided to house the composition, the container comprising a nozzle for spraying the composition. According to other embodiments, the composition comprises a grease or gel in which the oligomers are dispersed.

According to certain embodiments, the composition may further comprise a plurality of particles or molecules which provide an optical signature. For example, the plurality of particles or molecules may provide a range of refractive properties which can be scanned and used to identify the composition. According to embodiments, nanoparticle such an inorganic ceramic powder may be dispersed in the composition. A range of different powders provide a range of distinct optical signatures which can be used to identify the composition. The range of unique optical signatures will generally be less than the range of different nucleotide sequences. As such, the optical signature may not uniquely label every different composition in practice. However, such an optical signature can be useful to identify a manufacturer of the compositions, a supplier, a source and/or batch of compositions.

In light of the above, it is evident that compositions according to embodiments of the present invention may provide a cascading range of different identification components and methods. At a top level, the composition may have a specific colour, e.g. a blue colour under fluorescent light. This may serve to identify a company using that colour. However, as more companies enter this field, it is likely that certain companies will end up using the same fluorescent colour for their identifier compositions. A second level of identification may be provided by way of microdots identifying the source of the compositions more precisely. However, if a sample of the composition does not contain a microdot then some other means is required to identify the source of the composition. A third level of identification may thus be provided by way of an optical signature using a plurality of optically active molecules or nanoparticles dispersed in the composition to identify the source of the composition. Finally, a fourth level of identification is provided by way of the nucleotide identifier sequences to precisely and uniquely identify each and every individual composition. Such a cascading range of identification methods provides a range of different levels of identification so as to ensure that identification will be successful. Furthermore, top level identification is made quick and cheap to perform without overly complex or expensive equipment allowing individuals or police forces to identify a central source for a composition. The more complex and time consuming nucleotide analysis can thus be centralized.

The compositions will generally be manufactured by forming the nucleotide oligomers and then dispersing them in a suitable medium for deployment, e.g. as an adhesive, grease, gel or spray. The compositions will then be loaded into suitably coded containers and a record made to link each coded container to its nucleotide code. When sold to a customer, details of the custom are taken along with the code of the purchased container. Thus, the customer's details can be tied to the nucleotide code in a database as described in the background section.

According to embodiments of the present invention, the nucleotide oligomers may comprise DNA or RNA. DNA is preferred as it is more stable. The nucleotide oligomers may be single stranded or double stranded. Single stranded nucleotide oligomers are preferred according to some applications because they are cheaper to manufacture. However, while double stranded oligomers are more expensive to manufacture they do have the advantageous feature that they are more stable than single stranded oligomers. Accordingly, in some applications double stranded oligomers may be preferred.

According to another aspect of the present invention a plurality of containers of the composition are provided. Each container is identifiable by a unique combination of the first and second identifier sequences. The containers may be grouped in batches, wherein the first identifier is for identifying the batch to which a container belongs and the second identifier is for uniquely identifying each container within said batch.

According to another aspect of the invention a security marking kit is provided, the kit comprising:

(1a) a security marking composition comprising a plurality of identical first synthetic nucleotide oligomers; and a plurality of identical second synthetic nucleotide oligomers which are different to the first synthetic nucleotide oligomers, wherein each of the first synthetic nucleotide oligomers comprises a first primer binding sequence of bases, a first identifier sequence of three to seven bases in length, and a second primer binding sequence of bases, the first identifier sequence being disposed between the first and second primer binding sequences, wherein each of the second synthetic nucleotide oligomers comprises a third primer binding sequence of bases, a second identifier sequence of three to seven bases in length, and a fourth primer binding sequence of bases, the second identifier sequence being disposed between the third and fourth primer binding sequences, wherein the first identifier sequence is different to the second identifier sequence; and/or (1b) a pressurized container housing the composition of (a), and further comprising at least one of a solvent and a propellant, the pressurized container comprising a nozzle for spraying said composition; and (2) instructions for recording ownership of the kit in a database.

According to another aspect of the present invention, the composition is used in security marking of property and/or for marking a thief or attacker.

According to another aspect of the present invention, there is provided a method of determining an owner of a composition as described herein, the method comprising: taking a sample of the composition; reacting one or both of the first and second synthetic nucleotide oligomers with primers which bind to the first and second and/or third and fourth primer binding sequences to increase the length of one or both of the first and second synthetic nucleotide oligomers; amplifying one or both of the first and second synthetic nucleotide oligomers using a polymerase chain reaction; sequencing the amplified synthetic nucleotide oligomers to identify the first and/or second identifier sequence; and consulting a database to match the identified first and/or second identifier sequence with information about the owner of the composition.

The primers may comprise primer sequences which are standard primer sequences used in Sanger amplification and sequencing. The primers are longer than the primer binding sequences in order to improve sequencing accuracy. For example, the primers may have a length in the range 50 to 200 bases, preferably 50 to 100 bases.

BRIEF DESCRIPTION OF THE DRAWINGS

For a better understanding of the present invention and to show how the same may be carried into effect, embodiments of the present invention will now be described by way of example only with reference to the accompanying drawings, in which.

DESCRIPTION OF THE PREFERRED EMBODIMENTS OF THE INVENTION

Figure 1:
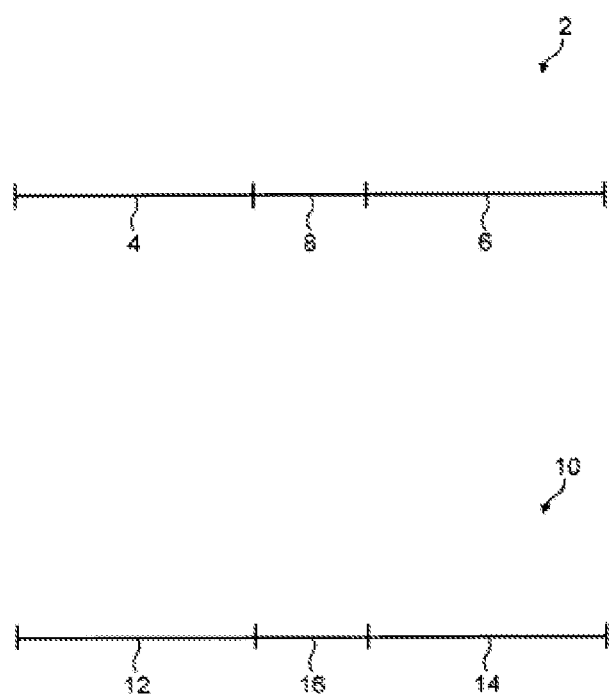
FIG. 1 shows a schematic illustration of first and second synthetic nucleotide oligomers in accordance with an embodiment of the present invention.

Compositions of the present invention comprise a mixture of two different synthetic nucleotide oligomers. Examples are illustrated in FIG. 1. The first synthetic nucleotide oligomer 2 comprises a primer binding sequence 4, a primer binding sequence 6, and an identifier sequence 8 disposed between the primer binding sequences. The second synthetic nucleotide oligomer 10 is similar in structure to the first oligomer and comprises a primer binding sequence 12, a primer binding sequence 14, and an identifier sequence 16 disposed between the primer binding sequences.

The identifier sequences are used to identify the composition. The identifier sequences of the two oligomers are different and together provide a unique code for the composition. The identifier sequences have three to seven bases, preferably 4 to 6 bases. The primer binding sequences are identical or complementary to portions of standard primer sequences used for amplifying the oligomer during analysis.

Figure 2:
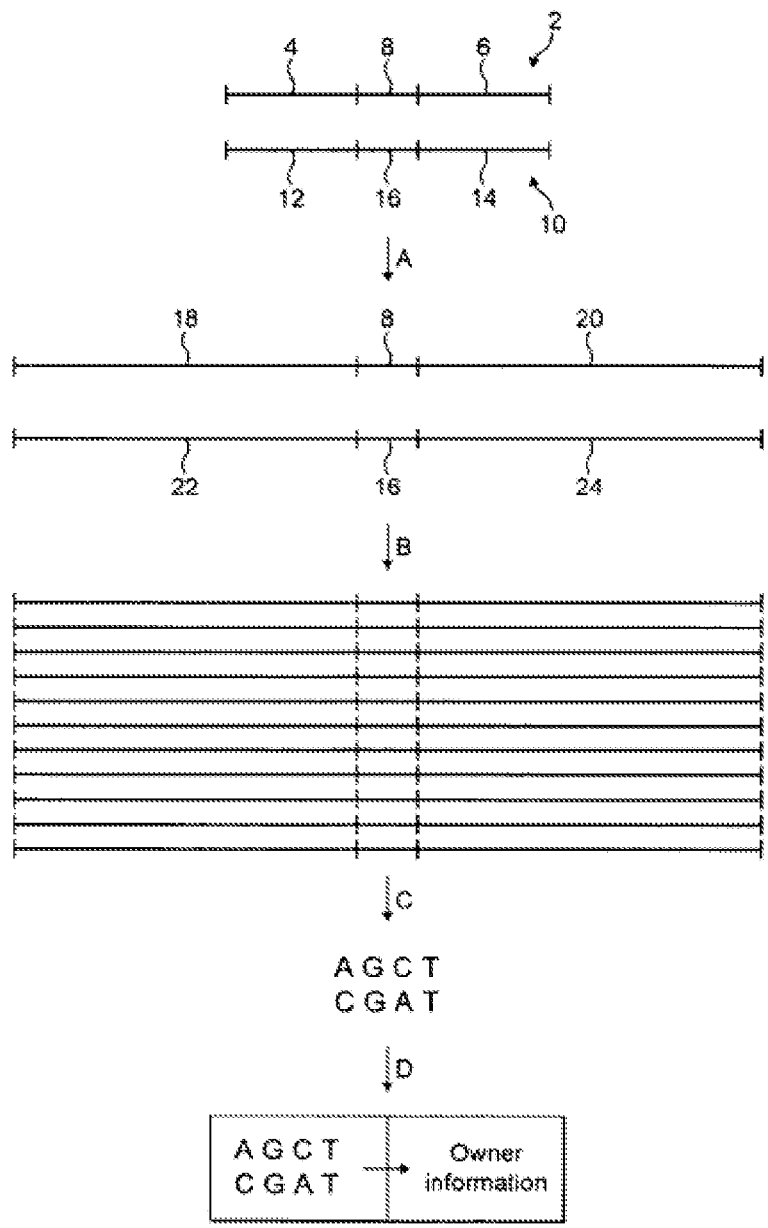
FIG. 2 shows a schematic illustration of a method of determining an owner of a composition in accordance with an embodiment of the present invention.

FIG. 2 shows a method of analyzing a composition comprising a mixture of two different synthetic nucleotide oligomers 2, 10 as described above in relation to FIG. 1.

A sample of the composition is taken and the nucleotide oligomers are isolated. The nucleotide oligomers are then lengthened using primers and then amplified using a polymerase chain reaction. One key feature is that the primers are longer than the primer binding sequences of the nucleotide oligomers 2, 10. Accordingly, the nucleotide oligomers are increased in length as illustrated in Step A of FIG. 2. The extended oligomers retain the same length of identifier sequence 8, 16 but have much longer primer sequences 18, 20, 22, 24 when compared to the original primer binding sequences 4, 6, 12, 14. These extended oligomers are amplified in number using a polymerase chain reaction as illustrated in Step B and then sequenced as illustrated in Step C. The longer oligomers can be sequenced using standard sequencing methods. In contrast, it would be difficult to sequence the shorter oligomers accurately using standard methods. Finally, in Step D a database is used to match the identified sequences with information about the owner of the composition.

Figure 3:
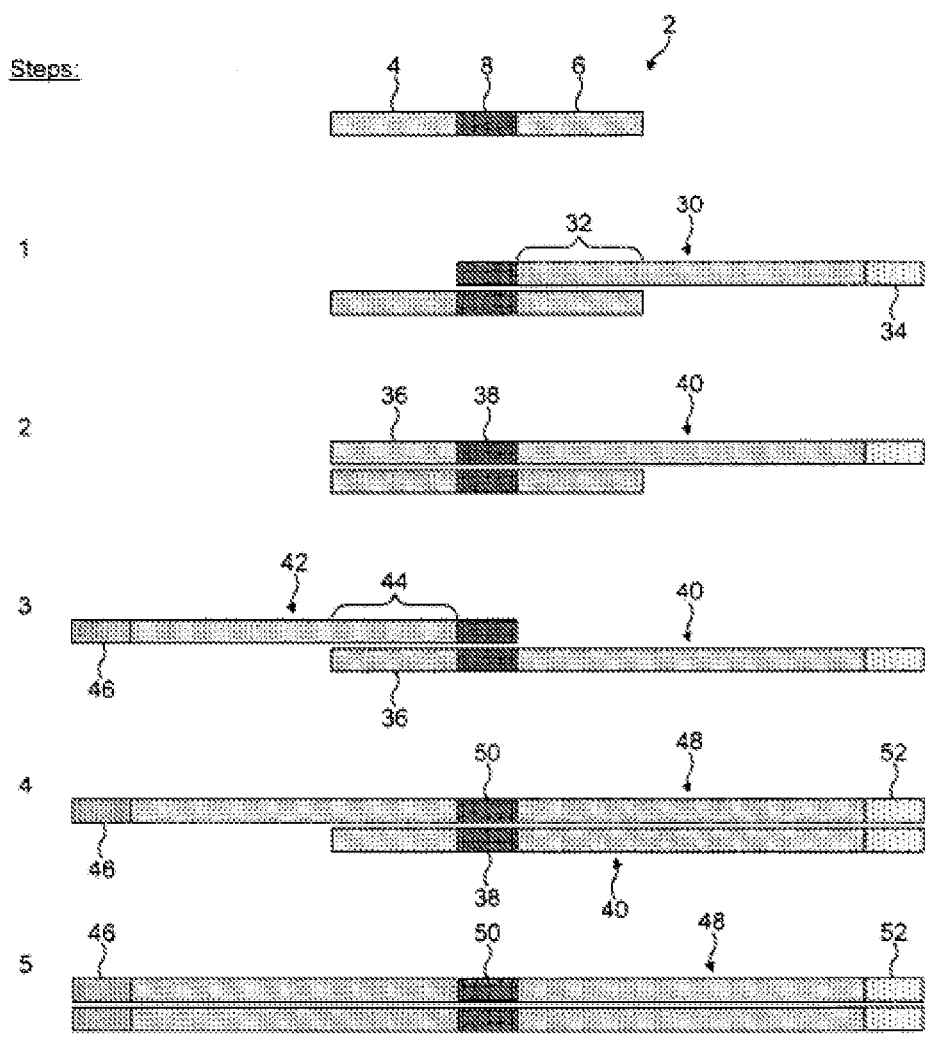
FIG. 3 shows a schematic illustration of a method used to lengthen and amplify one of the nucleotide oligomers in accordance with an embodiment of the present invention.

FIG. 3 shows in more detail a method used to lengthen and amplify one of the nucleotide oligomers. As before, the synthetic nucleotide oligomer 2 comprises a first primer binding sequence 4, a second primer binding sequence 6, and an identifier sequence 8 disposed between the primer binding sequences.

In Step 1, a PCR primer 30 is bound to the second primer binding sequence 6. The PCR primer 30 has a terminal portion 32 at its 3' end which is complementary to the second primer binding sequence 6 for binding thereto. The PCR primer 30 also has a primer binding site 34 for Sanger sequencing amplification at a position other than the terminal portion 32. In this case, the primer binding site 34 is at the 5' end of the PCR primer 30 and comprises a sequence corresponding to a reverse sequence primer.

In Step 2, the PCR primer sequence 30 is extended using the synthetic nucleotide oligomer 2 as a template so as to form an extended sequence 40 comprising portions 36 and 38 which are complementary to the first primer binding sequence 4 and the identifier sequence 8 of the original synthetic nucleotide oligomer 2.

In Step 3, a second PCR primer 42 is bound to the portion 36 of the extended sequence 40. The second PCR primer 42 has a terminal portion 44 at its 3' end which is complementary to the portion 36 of the extended sequence 40. As the portion 36 is complementary to the first primer binding sequence 6, then the terminal portion 44 of the second primer 42 is identical to the original first primer binding sequence 4.

The second PCR primer 42 also has a primer binding site 46 for Sanger sequencing amplification at a position other than the terminal portion 44. In this case, the primer binding site 46 is at the 5' end of the PCR primer 42 and comprises a sequence corresponding to a forward sequence primer.

In Step 4, the second PCR primer 42 is extended using the extended sequence 40 as a template so as to form a final extended sequence 48 comprising portion 50 which is complementary to portion 38 and thus identical to the identifier sequence 8 of the original synthetic nucleotide oligomer 2. The final extended sequence 48 thus comprises a sequence of a forward sequence primer 46, a sequence of a reverse sequence primer 52, and a sequence 50 identical to the identifier sequence 8 of the original synthetic nucleotide oligomer 2.

In Step 5, the final extended sequence 48 is amplified in number using PCR amplification. The amplification product can then be sequenced using the forward and reverse sequencing primer sites.

The same method steps can be utilized for amplification and sequencing of a second nucleotide oligomer in the composition using a third and fourth PCR primer. In this case, if the first and second PCR primers harbour the same sequencing primer binding sites as the third and fourth PCR primers respectively, the nucleotide oligomers should be amplified and sequenced separately. Alternatively, if the first and second PCR primers harbour different sequencing primer binding sites to the third and fourth PCR primers respectively, the nucleotide oligomers may be amplified in one reaction. However, sequencing analysis should still be performed separately.

The compositions and methods of the present invention allow short nucleotide oligomers to be utilized for uniquely identifying the compositions while enabling standard equipment to be utilized for sequencing the oligomers by extending the length of the oligomers during the initial stages of amplification.

While this invention has been particularly shown and described with reference to preferred embodiments, it will be understood to those skilled in the art that various changes in form and detail may be made without departing from the scope of the invention as defined by the appending claims.

The invention claimed is:

1. A system comprising a security marking composition and a database, wherein the security marking composition comprises:
    a plurality of identical first synthetic nucleotide oligomers; and
    a plurality of identical second synthetic nucleotide oligomers which are different to the first synthetic nucleotide oligomers,
    wherein each of the first synthetic nucleotide oligomers consists of a first primer binding sequence of bases, a first identifier sequence of three to seven bases in length, and a second primer binding sequence of bases, the first identifier sequence being disposed between the first and second primer binding sequences,
    wherein each of the second synthetic nucleotide oligomers consists of a third primer binding sequence of bases, a second identifier sequence of three to seven bases in length, and a fourth primer binding sequence of bases, the second identifier sequence being disposed between the third and fourth primer binding sequences,
    wherein the first and second primer binding sequences are different to each other and to each of the third and fourth primer binding sequences,
    wherein the first identifier sequence is different to the second identifier sequence,
    wherein the database connects information on an owner of the composition to the first and second identifier sequences, and
    wherein the security marking composition further comprises one or more of a fluorescent material, a plurality of microdots, a propellant, a grease and/or a gel.

2. A system according to claim 1, wherein the first identifier sequence has a length in the range four to six bases.

3. A system according to claim 1, wherein the second identifier sequence has a length in the range four to six bases.

4. A system according to claim 1, wherein the third and fourth primer binding sequences are different.

5. A system according to claim 1, wherein the first, second, third and fourth primer binding sequences each have a length in the range 5to 40 bases.

6. A system according to claim 5, wherein the first, second, third and fourth primer binding sequence each have a length in the range of 10 to 30 bases.

7. A security marking composition, wherein the security marking composition comprises:
    a plurality of identical first synthetic nucleotide oligomers; and
    a plurality of identical second synthetic nucleotide oligomers which are different to the plurality of identical first synthetic nucleotide oligomers,
    wherein each of the plurality of identical first synthetic nucleotide oligomers consists of a first primer binding sequence of bases, a first identifier sequence of three to seven bases in length, and a second primer binding sequence of bases, the first identifier sequence being disposed between the first and second primer binding sequences,
    wherein each of the plurality of identical second synthetic nucleotide oligomers consists of a third primer binding sequence of bases, a second identifier sequence of three to seven bases in length, and a fourth primer binding sequence of bases, the second identifier sequence being disposed between the third and fourth primer binding sequences,
    wherein the first and second primer binding sequences are different to each other and to each of the third and fourth primer binding sequences,
    wherein the first identifier sequence is different to the second identifier sequence,
    wherein information on an owner of the composition is provided by the first and second identifier sequences using a database which connects information on an owner of the composition to the first and second identifier sequences, and
    wherein the security marking composition further comprises one or more of a fluorescent material, a plurality of microdots, a propellant, a grease and/or a gel.

8. A pressurized container housing the composition according to claim 7, the composition comprising the propellant, the pressurized container comprising a nozzle for spraying said composition.

9. A plurality of containers, each container comprising a composition according to claim 7, wherein each container is identifiable by a unique combination of the first and second identifier sequences.

10. A plurality of containers according to claim 9, comprising a plurality of batches of containers, wherein the first identifier is for identifying the batch to which a container belongs and the second identifier is for uniquely identifying each container within said batch.

11. A security marking kit, the kit comprising:
    (1) a security marking composition according to claim 7 and/or a pressurized container housing the security marking composition along with a propellant and a nozzle for spraying said composition; and
    (2) instructions for recording ownership of the kit in a database.

12. The security marking composition of claim 7, further comprising an adhesive.

13. A method of determining an owner of a security composition, the method comprising:
    taking a sample of the security composition;
    reacting one or both of the first and second synthetic nucleotide oligomers with primers which bind to the first and second and/or third and fourth primer binding sequences to increase the length of one or both of the first and second synthetic nucleotide oligomers;

amplifying one or both of the first and second synthetic nucleotide oligomers using a polymerase chain reaction;

sequencing the amplified synthetic nucleotide oligomers to identify the first and/or second identifier sequence; and consulting a database to match the identified first and/or second identifier sequence with information about the owner of the composition, wherein the database connects information on the owner of the composition to the first and second identifier sequence;

wherein the security marking composition comprises:

a plurality of identical first synthetic nucleotide oligomers; and a plurality of identical second synthetic nucleotide oligomers which are different to the first synthetic nucleotide oligomers, wherein each of the first synthetic nucleotide oligomers consists of a first primer binding sequence of bases, a first identifier sequence of three to seven bases in length, and a second primer binding sequence of bases, the first identifier sequence being disposed between the first and second primer binding sequences, wherein each of the second synthetic nucleotide oligomers consists of a third primer binding sequence of bases, a second identifier sequence of three to seven bases in length, and a fourth primer binding sequence of bases, the second identifier sequence being disposed between the third and fourth primer binding sequences, wherein the first and second primer binding sequences are different to each other and to each of the third and fourth primer binding sequences, wherein the first identifier sequence is different to the second identifier sequence, wherein information on an owner of the composition is provided by the first and second identifier sequences using a database which connects information on an owner of the composition to the first and second identifier sequences.

14. A method according to claim 13, wherein the primers have a length in the range 50 to 200 bases.

15. A method according to claim 14, wherein the primers have a length in the range of 50 to 100 bases.

* * * * *